United States Patent [19]

Getman et al.

[11] Patent Number: 5,026,713
[45] Date of Patent: * Jun. 25, 1991

[54] 1,3-DIDEOXY-3-FLUORONOJIRIMYCIN WHICH INHIBITS GLYCOSIDASE ACTIVITY

[75] Inventors: Daniel P. Getman, St. Louis; Gary A. DeCrescenzo, St. Peters, both of Mo.

[73] Assignee: Monsanto Company, St. Louis, Mo.

[*] Notice: The portion of the term of this patent subsequent to Jun. 18, 2008 has been disclaimed.

[21] Appl. No.: 400,252

[22] Filed: Aug. 29, 1989

[51] Int. Cl.$^5$ .............. C07D 211/42; C07D 491/056
[52] U.S. Cl. ................................. 514/302; 514/315; 514/328; 546/116; 546/219; 546/220; 546/242
[58] Field of Search .............. 546/116, 219, 220, 242; 514/328, 315, 302

[56] References Cited

U.S. PATENT DOCUMENTS 4,348,402 9/1982 Kinast et al. .................. 546/198

FOREIGN PATENT DOCUMENTS 3620645 7/1987 Fed. Rep. of Germany.

Primary Examiner—Bernard Dentz
Attorney, Agent, or Firm—Charles E. Smith; James W. Williams, Jr.; James C. Bolding

[57] ABSTRACT

Novel compounds represented by the formula:

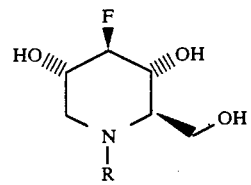

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms and optionally substituted acyl and acyloxy radicals having from about 1 to about 10 carbon atoms, manifest glycosidase inhibition activity.

27 Claims, No Drawings

1,3-DIDEOXY-3-FLUORONOJIRIMYCIN WHICH INHIBITS GLYCOSIDASE ACTIVITY

BACKGROUND OF THE INVENTION

1. Field of the Invention

This invention relates to novel piperidine derivatives which manifest glycosidase inhibition activity and to novel intermediates useful in the manufacture thereof. The present invention also relates to methods for preparing such derivatives and intermediates.

More particularly, the present invention relates to 4-fluoro analogs of 2-hydroxymethyl-3, 5,-dihydroxypiperidines, which are the ring nitrogen analogs of 1-deoxy-D-glucose and are generally referred to as 1-deoxynojirimycin (DNJ) analogs. More particularly, the present invention relates to 1,3-dideoxy-3-fluoronojirimycin and the corresponding N-derivatives; to intermediates useful in preparing such fluorinated analogs; to methods for preparing the intermediates beginning with 1-deoxynojirimycin as starting material; and to methods for preparing the 3-fluoro analogs utilizing such intermediates.

2. Related Art

1-Deoxynojirimycin is a known glucosidase inhibitor. See, for example, Truscheit et al., Ang. Chemie Int'l. Ed., 20, 744 (1981). Fluoro analogs of glucose and glucose derivatives are also known. For example, see Withers et al, J. Amer. Chem. Soc., 109, 7530-31 (1987), and "Fluorinated Carbohydrates: Chemical and Biochemical Aspects; ACS Symposium Series 184," ed. N. F. Taylor, American Chemical Society (1988).

Kinast et al, DE3620645, disclose 2-amino-1-deoxynojirimycin derivatives which inhibit glucosidases. A cyclic stannylene intermediate of 1-deoxymannojirimycin is utilized to specifically functionalize the 3-hydroxy group.

Munava et al, J. Org. Chem., 41, 1832 (1976), disclose a cyclic stannylene intermediate of glucose utilized to functionalize the 2-hydroxy group with a benzoyl group.

David et al, Tetrahedron, 41(4), 643 (1985) review utilization of stannylenes in carbohydrate chemistry.

SUMMARY OF THE INVENTION

The present invention is directed at 1,3-dideoxy-3-fluoronojirimycin, and the N-derivatives thereof. These compounds are prepared utilizing novel N-substituted-4,6-O-benzylidene-1,3-dideoxy-3-fluoronojirimycin intermediates, N-substituted-4,6-O-benzylidene-2-O-substituted-1-deoxynojirimycin intermediates, N-substituted-2-O-substituted-4,6-O-benzylidene-3-keto-1-deoxynojirimycin, N-substituted-2-O-substituted-4,6-O-protected-1-deoxyallojirimycin, and N-substituted-2,3-O-(dialkylstannylene)-4,6-O-benzylidene-1-deoxynojirimycin intermediates which are utilized to produce the subject compounds.

DETAILED DESCRIPTION OF THE INVENTION

The present invention resides in the discovery that novel 3-deoxy-3-fluoro analogs of 1-deoxynojirimycin and the N-derivatives thereof manifest glycosidase inhibition activity. The subject compounds can be represented by the formula:

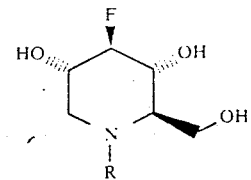

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms, and optionally substituted acyl and acyloxy radicals having from about 1 to about 10 carbon atoms. Accordingly, the present invention is directed to such novel analogs, to novel intermediates useful in the manufacture of such analogs, and to methods for preparing such novel intermediates and analogs.

These novel analogs and intermediates can be represented generically by the formula:

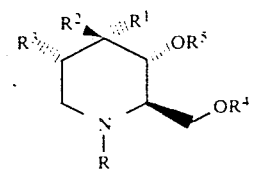

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms and optionally substituted acyl and acyloxy radicals having from about 1 to about 10 carbon atoms; $R^1$ represents hydrogen and a hydroxyl group; $R^2$ represents hydrogen and fluorine or together with $R^1$ represent a keto group; $R^3$ represents hydroxy, substituted and unsubstituted benzyl and allyl ethers, and acyl esters represented by the following formula:

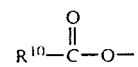

wherein $R^{10}$ represents optionally substituted alkyl radicals having from 1 to about 10 carbon atoms and optionally substituted aryl, aralkyl and alkaryl radicals or together with $R^2$ represents a cyclic stannylene derivative of the formula

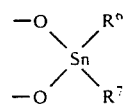

wherein $R^6$ and $R^7$ independently represent alkyl radicals having from 1 to about 10 carbon atoms; provided that when $R^2$ is fluorine, $R^3$ is hydroxy, substituted or unsubstituted benzyl or allyl ether, or acyl ester; and $R^4$ and $R^5$ represent hydrogen and hydroxy protecting groups.

More particularly, the novel analogs can be represented by the formula:

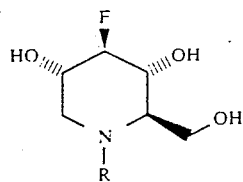

wherein R represents hydrogen, optionally substituted alkyl radicals having from 1 to about 10 carbon atoms, optionally substituted alkenyl radicals having from 1 to about 10 carbon atoms, optionally substituted aryl, alkaryl and aralkyl radicals having from about 6 to about 16 carbon atoms and optionally substituted acyl and acyloxy radicals having from about 1 to about 10 carbon atoms.

The N-substituted-4,6-O-protected-1, 3-dideoxy-3-fluoronojirimycin intermediates can be represented by the formula:

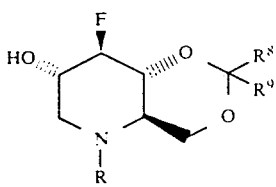

wherein R has the same meaning as set forth above and $R^8$ and $R^9$ independently represent hydrogen, substituted and unsubstituted alkyl radicals having from 1 to about 10 carbon atoms and substituted and unsubstituted aryl radicals.

The N-substituted-2-O-substituted-1,3-dideoxy-3-fluoronojirimycin can be represented by the formula:

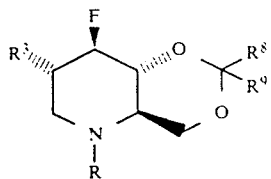

wherein R, $R^3$, $R^8$ and $R^9$ have the same meaning as set forth above.

The N-substituted-2-O-substituted-4,6-O-protected-1-deoxyallojirimycin can be represented by the formula:

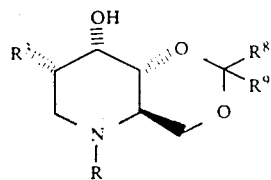

wherein R, $R^3$, $R^8$ and $R^9$ have the same meaning as set forth above.

The N-substituted-2-O-substituted-4,6-O-benzylidene-3-keto-1-deoxynojirimycin can be represented by the formula:

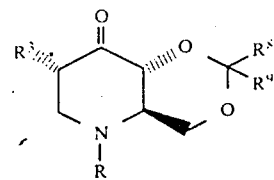

wherein R, $R^3$, $R^8$ and $R^9$ have the same meaning as set forth above.

The 2-O-substituted intermediates can be represented by the formula:

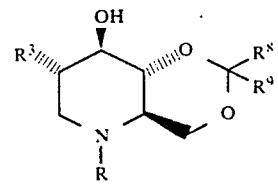

wherein R has the same meaning as set forth above; $R^3$ represents substituted and unsubstituted benzyl and allyl ethers, substituted and unsubstituted acyl esters represented by the formula:

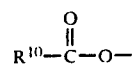

wherein $R^{10}$ represents optionally substituted alkyl radicals having from 1 to about 10 carbon atoms and optionally substituted aryl, aralkyl and alkaryl radicals; and $R^8$ and $R^9$ have the same meaning as set forth above.

The cyclic stannylene intermediates can be represented by the formula:

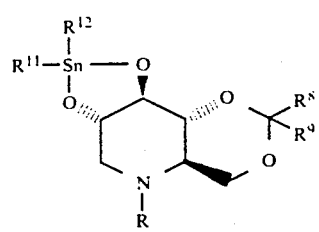

wherein R, $R^8$ and $R^9$ represent radicals as defined above; and $R^{11}$ and $R^{12}$ represent alkyl radicals having from 1 to about 10 carbon atoms.

The 1,3-dideoxy-3-fluoronojirimycin compound of the present invention can be prepared beginning with 1-deoxynojirimycin (hereinafter referred to as "DNJ"), which can be prepared by known procedures as disclosed in U.S. Pat. Nos. 4,220,782; 4,246,345; and 4,806,650. The corresponding N-alkyl derivatives can then be prepared according to known procedures. See, for example, U.S. Pat. Nos. 4,220,782; 4,266,025; 4,405,714; and 4,806,650.

Starting with DNJ, the N-alkyl group can first be introduced according to known procedures. The 4-hydroxy and 6-hydroxy groups are then protected by techniques well known to those familiar with carbohydrate chemistry. These N-alkyl-4,6-O-protected derivatives can be represented by the formula:

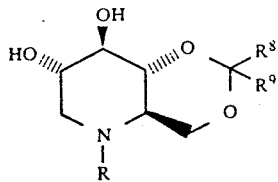

wherein $R^8$ and $R^9$ independently represent radicals as defined above. For example, utilizing 2,2-dimethoxypropane or, preferably, benzaldehyde, the corresponding 4,6-O-isopropylidene- ($R^8=R^9=CH_3$) or 4,6-O-benzylidene ($R^8=$phenyl, $R^9=H$) N-substituted DNJ can be produced. These reactions are generally conducted in an inert organic solvent and in the presence of a strong acid which acts as catalyst. The reactions can be conducted at temperatures of from about 0° C. to about 50° C., preferably from about 10° C. to 40° C., such as from about 20° C. to about 30° C. Exemplary acid catalysts include zinc chloride, p-toluenesulfonic acid and the like. During the reaction water is removed, preferably utilizing a molecular sieve such as a 3 angstrom (Å) molecular seive.

Alternatively, starting with DNJ, the amino group can be protected and then the 4-hydroxy and 6-hydroxy groups are protected according to the above procedure. Protection of the amino group can be accomplished by methods well known to those familiar with amino acid chemistry. For example, the amino group can be protected utilizing a carbonyl compound represented by the formula

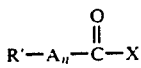

wherein R' represents alkyl radicals having from 1 to about 10 carbon atoms, and aryl, aralkyl and alkaryl radicals having from about 6 to about 26 carbon atoms; or aryl or alkylaryl or araalkyl with suitable carbon numbers, A represents oxygen; n is 0 or 1; and X represents Cl, Br, I, or $C(O)A_nR'$ wherein R', A and n have the same meanings as defined above. Exemplary amino protecting groups include carbobenzoxy, butyryl, benzoyl, and the like. These reactions are generally conducted in a polar solvent and in the presence of a base at a temperature of from about 0° C. to about 50° C., preferably from about 0° C. to about 25° C. such as from about 10° C. to 20° C. Exemplary bases include $NaHCO_3$, NaOH and certain tertiary amines. Exemplary solvents include water and N,N-dimethylformamide.

It is preferred, however, that the compounds of the present invention be prepared starting with DNJ, protecting the amino group with the carbobenzoxy group and then protecting the 4-hydroxy and 6-hydroxy groups utilizing the benzylidene protecting group. Optionally, the amino protecting group can then be removed by procedures well known in the art, such as with a base, e.g., KOH, NaOH, and LiOH. In this case, an alkyl acid chloride is then reacted with the 4,6-O-benzylidene-1-deoxynojirimycin to produce the N-carboalkyl-4,6-O-benzylidene-1-deoxynojirimycin, the N-carboalkyl being reduced to the desired alkyl group in a subsequent step as discussed below. Alternately, the amino protecting group can be removed in a later step as discussed below.

In order to facilitate discussion of the remaining method steps, the N-alkyl, N-carboaryloxy, N-carboalkyloxy, and N-carboalkyl DNJ derivatives will be collectively referred to as N-protected. Also, the 4,6-O-benzylidene and the like compounds will be referred to as 4,6-O-protected compounds.

The above-described N-protected-4,6-O-protected-1-deoxynojirimycin is then reacted with a dialkyltin oxide ($R^{11}R^{12}SnO$), preferably di-n-butyltin oxide, in a suitable solvent such as methanol, benzene or toluene to form the novel corresponding cyclic stannylene derivative represented by the formula:

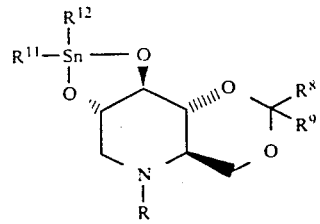

wherein R, $R^8$ and $R^9$ have the same meaning as set forth above and $R^{11}$ and $R^{12}$ independently represent alkyl radicals having from 1 to about 10 carbon atoms, such as from about 1 to about 6 carbon atoms, preferably about 4 carbon atoms.

The cyclic stannylene derivative is then reacted with a suitable agent for providing the desired acyl ester, benzyl or allyl ether derivatives. These derivatives are referred to herein as 2-O-substituted derivatives. Suitable acylating agents include those represented by the formula:

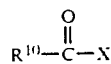

wherein X represents Cl, Br, I, and

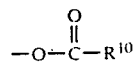

and $R^{10}$ represents optionally substituted alkyl radicals having from 1 to about 10 carbon atoms and optionally substituted aralkyl and aryl radicals. Exemplary $R^{10}$ radicals include phenyl, p-methylphenyl, chloromethyl and methyl. A preferred acylating agent is benzoyl chloride. Exemplary bases include tertiary amines such as triethylamine, and diisopropylethyl amine, pyridine, N,N-dimethylaminopyridine, 1,8-diazabicyclo[5.4.0]undec-7-ene (DBU) and 1,5-diazabicyclo[4.3.0]non-5-ene (DBN). Suitable benzylating agents include benzyl triflate and benzyl halides, e.g., benzyl chloride, bromide and iodide. Suitable allylating agents include allyl halides such as allyl bromide and allyl iodide. The benzylation and allylation reactions are conducted in the presence of a catalytic amount of a tetraalkylammonium iodide, for example, tetra-n-butyl ammonium iodide, in a suitable solvent such as THF, acetonitrile or N,N-dimethylformamide. The reactions are conducted in an inert solvent in the presence of a base and at a temperature of between about 0° C. and 100° C., preferably at a temperature of from about 0° C. to about 25° C.

The resulting novel product of the reaction between the cyclic stannylene and the acylating, benzylating or allylating agent is predominantly the N-protected-2-O- substituted-4,6-O-benzylidene-1-deoxynojirimycin represented by the formula:

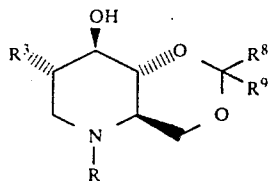

wherein R³ represents an acyl ester as defined above and R, R⁸ and R⁹ are as defined above. By predominant it is meant that the 2-O-substituted product is produced in excess of the 3-O-substituted product.

The N-protected-2-O-substituted-4,6-O-benzylidene-1-deoxynojirimycin is then oxidized and reduced under conditions which produce the corresponding N-protected-2-O-substituted-4,6-O-benzylidene-1-deoxyallojirimycin represented by the formula:

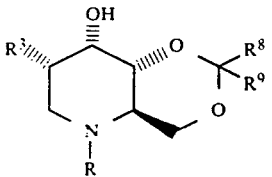

wherein R, R³, R⁸ and R⁹ are as defined above.

For example, oxidation can be effected utilizing a variety of oxidizing agents, for example, pyridinium chlorochromate, pyridinium dichromate and the like. Preferred oxidizing agents are those referred to as Swern reagents by those skilled in the art. Swern reagents, generally are combinations of dimethyl sulfoxide and either trifluoroacetic anhydride or oxalyl chloride, and triethylamine. The reaction is conducted in an inert solvent at a temperature of from about −80° C. to about 30° C. A preferred inert solvent is methylene chloride. For a review of these Swern reagents, see A. J. Mancuso and D. Swern, Synthesis, 165 (1981) which is herein incorporated by reference. A preferred inert solvent is methylene chloride.

The resulting ketone, represented by the formula:

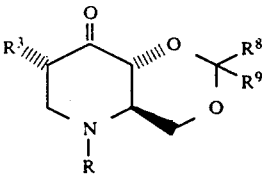

wherein R, R³, R⁸ and R⁹ are as defined above, is then reduced utilizing a metal borohydride such as sodium, lithium and potassium borohydride, in the presence of THF and methanol or with an alumino hydride, such as lithium trialkylaluminohydride and lithium trialkoxyaluminohydride, in THF, and at a temperature of from about −80° C. to about 30° C. The resulting reduced product is the N-protected-2-O-substituted-4,6-O-benzylidene-1-deoxyallojirimycin described above.

The N-protected-2-O-substituted-4,6-O-benzylidene-1-deoxyallojirimycin is then reacted with a suitable fluorine source with inversion of configuration at C-3 to produce the corresponding N-protected-2-O-substituted-4,6-O-benzylidene-1,3-dideoxy-3-fluoronojirimycin represented by the formula:

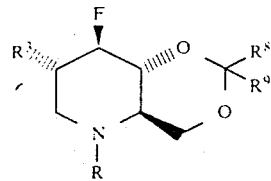

wherein R, R³, R⁸ and R⁹ are as defined above. The reaction is preferably conducted in an inert-solvent, e.g., methylene chloride, benzene, toluene, chloroform, THF, and the like, at a temperature of between about −80° C. and about 120° C., preferably between about 0° C. and about 85° C. Exemplary fluorine sources include those represented by the formula:

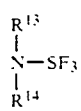

wherein $R^{13}$ and $R^{14}$ independently represent optionally substituted alkyl groups having from 1 to about 6 carbon atoms. A preferred alkyl group is ethyl.

Alternatively, the inverted alcohol can first be activated by conversion to its trifluoromethanesulfonate or p-methylbenzenesulfonate derivative and then displaced by a fluoride source in a suitable solvent. Suitable fluoride sources include cesium fluoride, potassium hydrogen fluoride, tetraalkylammonium fluorides, e.g., tetra-n-butylammonium fluoride, and tris(dimethylamino)sulfur (trimethylsilyl)difluoride. Suitable solvents include acetonitrile and N,N-dimethylformamide. This reaction is conducted at a temperature of between about −80° C. and 120° C.

The next step involves removal of the acyl, benzyl or allyl group at C-2. These groups can be removed in a variety of ways well known to those skilled in the art. For example, the acyl groups can be removed utilizing lithium hydroxide, sodium hydroxide or potassium hydroxide in aqueous tetrahydrofuran. A preferred method for removal utilizes sodium methoxide in methanol.

The next step involves removal of the 4,6-O-protecting group, e.g., the benzylidene group, by methods well known to those skilled in the art. Generally, such protecting groups can be removed utilizing an acid in an appropriate solvent at room temperatures. For example, $CF_3CO_2H$ in water, $CH_3CO_2H$ in water or HCl in water can be utilized to effectively deprotect the 4- and 6-hydroxy groups. Alternatively, such protecting groups can be removed catalytically. For example, reaction with palladium on carbon at 50° C. and 50 psi $H_2$.

It should be noted that where the amino protecting group can be removed through hydrogenolysis (for example, a carbobenzoxy group), hydrogenation in the presence of palladium on carbon will remove both the nitrogen protecting group and the 4,6-O-benzylidene protecting group. Thus, deprotection can occur in one step.

Alternatively, the acyl group can be reduced utilizing borane:dimethylsulfide, lithium aluminum hydride or diborane in a suitable solvent, e.g., THF, at a temperature of from about 0° C. to about 120° C., preferably from about 0° C. to about 25° C. A preferred reducing agent is borane:dimethylsulfide Following reduction of the acyl group to the corresponding alkyl group, the 4- and 6-hydroxy protecting groups can be removed as described above.

Where other amino protecting groups are utilized, however, one can remove such groups either prior to or following deprotection of the 4-and 6-hydroxy groups utilizing well known methods and, if desired, replace such groups with an appropriate alkyl group by methods well known in the art.

The subject 1,3-dideoxy-3-fluoronojirimycin and N-derivatives thereof manifest glycosidase inhibition activity. It is contemplated that certain intermediates disclosed herein will manifest similar activity. Thus, pharmaceutical compositions comprising one or more of the fluoro analogs and/or intermediates can be administered to a patient for this purpose. Such compositions, which may contain acceptable diluents and/or carriers, can be prepared by reference to general texts in the field such as, for example, *Remington's Pharmaceutical Sciences*, Ed. Arthur Osol, 16th ed., 1980, Mack Publishing Co.

Contemplated equivalents of the general formulas set forth above for the DNJ analogs and derivatives as well as the intermediates are compounds otherwise corresponding thereto and having the same general properties wherein one or more of the various R groups are simple variations of the substituents as defined therein, e.g., wherein R is a higher alkyl group. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. Methanol, toluene, benzaldehyde and triethylamine were dried over 3Å molecular sieves. Methylene chloride and tetrahydrofuran were purchased as anhydrous grade from Aldrich Chemical Co. and used as received. All proton and carbon NMR spectra were obtained on either a Varian VXR-300 or VXR-400 nuclear magnetic resonance spectrometer.

EXAMPLE 1

Preparation of N-Carbobenzoxy-4,6-O-benzylidene-1-deoxynojirimycin.

A total of 75.0 g (0.46 moles) of 1-deoxynojirimycin was dissolved in 1500 mL of saturated aqueous sodium bicarbonate and then treated with 73.5 mL (87.8 g, 0.52 moles) of 95% benzyl chloroformate at room temperature using an overhead stirrer under a nitrogen atmosphere for eighteen hours. The solution was extracted once with 250 mL of methylene chloride to remove any benzyl chloride and unreacted benzyl chloroformate. The aqueous solution was then extracted ten times with 500 mL of ethyl acetate. After drying over anhydrous magnesium sulfate, filtering and removal of solvent, 102.8 g (76% yield) of a colorless oil was obtained which was identified as N-carbobenzoxy-1-deoxynojirimycin of sufficient purity for use in the next step: 300 MHz $^1$H NMR (d, CD$_3$OD) 7.40-7.20 (m, 5H), 5.15 (s, 2H), 4.23 (br m, 1H), 4.05 (br d, J=8.0 Hz, 1H), 3.87 (dd, J=4.0 and 6.0 Hz, 1H), 3.85-3.78 (m, 2H), 3.78-3.70 (m, 2H), and 3.45 (br d, J=8.0 Hz, 1H).

To 102 g (0.345 mol) of N-carbobenzoxy-1-deoxynojirimycin, which had been dried in vacuo over phosphorous pentoxide overnight, was added 1000 mL of benzaldehyde (dried with 3 Å molecular sieves). This was warmed at 40° C. while swirling on a rotary evaporator (no vacuum) until the oil was fully dissolved, then split in half and each half transferred to a 5 L three-necked flask and an additional 200 mL of benzaldehyde used to rinse the flask and 100 mL added to each reaction. After placing each reaction flask under nitrogen, 101 g of freshly activated 3 Å molecular sieves were added and then 257.6 g of anhydrous zinc chloride (dried in vacuo overnight over P$_2$O$_5$) was added and some warming observed. After stirring for five hours at room temperature, 1000 mL of ethyl acetate was added, each flask cooled in an ice bath and then 1500 mL of a cold saturated aqueous solution of sodium bicarbonate was added. Some foaming was observed. The white precipitate which formed was filtered and washed with ethyl acetate. The filtrate was separated and the organic layer washed with saturated sodium chloride, dried with magnesium sulfate and filtered. The organic layers from each reaction were combined and stripped at 40° C. to afford a benzaldehyde solution of the desired product. This was then poured into 10 L of hexane with stirring, the precipitate collected and washed with hexane and air dried. This material was dissolved in approximately 1200 mL of hot ethyl acetate, hexane added to the cloud point (approx. 1500 mL), where-upon crystallization occurred. After cooling to room temperature, the precipitate was collected and washed well with hexane to afford 91.1 g (68%) of N-carbobenzoxy-4,6-O-benzylidene-1-deoxynojirimycin as a white solid, mp 147-148° C.; 300 MHz $^1$H NMR (d, CD$_3$OD) 7.53-7.28 (m, 10H), 5.61 (s, 1H), 5.14 (s, 2H), 4.77 (dd, J$_{5,6}$=4.6 Hz, J$_{6,6'}$=11.0 Hz, 1H,), 4.38 (t, J$_{5,6'}$=J$_{6,6'}$=11.0 Hz, 1 H$_{6'}$), 4.16 (dd, J$_{1,2}$=4.2 Hz, J$_{1,1'}$=13.4 Hz, 1H, H$_1$), 3.69-3.50 (complex m, 3H, H$_2$, H$_3$ and H$_4$), 3.35 (ddd, J$_{4,5}$=J$_{5,6'}$=11.0 Hz, J$_{5,6}$4.6 Hz, 1H, H$_5$) and 2.97 (dd, J$_{1',2}$=9.3 Hz, J$_{1,1'}$=13.4 Hz, 1H, H$_{1'}$); 75 MHz $^{13}$C NMR (CD$_3$OD) 156.7, 139.4, 138.0, 129.9, 129.7, 129.3, 129.2, 129.1, 127.6, 102.8, 81.9, 77.5, 71.5, 70.6, 68.6, 55.9 and 50.5 ppm; mass spectrum (m/e) 386 (M+H), 361, 327 and 280; and Anal. Calcd. for $C_{21}H_{23}NO_6$: C (65.45), H (6.01) and N (3.63); Found C (65.41), H (6.19) and N (3.59).

EXAMPLE 2

Preparation of N-Carbobenzoxy-4,6-O-benzylidene-2, 3-O-(di-n-butylstannylene)-1-deoxynojirimycin.

To a mixture of 0.50 g (1.30 mmol) of N-carbobenzoxy-4,6-O-benzylidene-1-deoxynojirimycin and 0.34 g (1.36 mmol) of di-n-butyltin oxide (both dried in vacuo over $P_2O_5$ overnight), under a nitrogen atmosphere, was added 5 mL of dry methanol (dried over 3Å molecular sieves) and the mixture refluxed for two hours. After cooling to room temperature, the volatiles were removed under vacuum, toluene added and then removed twice to afford N-carbobenzoxy-2,3-O-(di-n-butylstannylene)-4,6-O-benzylidene-1-deoxynojirimycin as a white solid; 300 MHz $^1$H NMR (d, $CDCl_3$) 7.50-7.25 (m, 10H), 5.42 (s, 1H), 5.05 (AB quartet, $J_{AB}=12.3$ Hz, $u_{AB}14.2$ Hz, 2H), 4.80 (dd, $J_{6,6'}=11.8$ Hz, $J_{5,6}=4.5$ Hz, 1H, $H_6$), 4.56 (dd, $J_{6,6'}=11.8$ Hz, $J_{5,6'}=11.4$ Hz, 1 H, $H_{6'}$), 4.39 (dd, $J_{1,1'}=12.7$ Hz, $J_{1,2}=4.1$ Hz, $H_1$), 3.51 (dd, $J_{3,4}=9.0$ Hz, $J_{4,5}=9.0$ Hz, 1H, $H_4$), 3.29 (ddd, $J_{5,6}=4.4$ Hz, $J_{4,5}=J_{5,6'}=10.5$ Hz, 1H, $H_5$), 3.17-3.03 (m, 2H, $H_2$ and $H_3$), 2.62 (dd, $J_{1,1'}=12.7$ Hz, $J_{1',2}=10.2$ Hz, 1H, $H_1'$) and 1.60-0.76 (m, 18H); and mass spectrum (m/e) 624 (M+Li).

EXAMPLE 3

Preparation of N-Carbobenzoxy-2-O-benzoyl-4,6-O-benzylidene-1-deoxynojirimycin

Method A.

A suspension of 30.0 g (77.8 mmol) of N-carbobenzoxy-4,6-O-benzylidene-1-deoxynojirimycin and 20.3 g (81.7 mmol) of di-n-butyltin oxide in 480 mL of dry toluene were heated with azeotropic removal of water for two hours, whereupon a homogeneous solution resulted. After cooling to room temperature, 9.43 g (93.4 mmol) of dry triethylamine and then 11.16 g (79.4 mmol) of benzoyl chloride were added. After stirring at room temperature for fifteen hours, an aqueous solution of saturated sodium bicarbonate was added, the solids filtered and washed with ethyl acetate. The filtrate was separated and the organic layer washed with 1N hydrochloric acid, dried with magnesium sulfate, filtered and concentrated to afford 38.1 g of a white solid. This was recrystallized from hot methylene chloride and hexane to afford 24.6 g (67%) of N-carbobenzoxy-2-O-benzoyl-4,6-O-benzylidene-1-deoxynojirimycin, mp 120-121° C.; 300 MHz $^1$H NMR (d, $CDCl_3$) 7.99 (d, J=7.7 Hz, 2H), 7.57 (t, J=7.7 Hz, 1H), 7.52-7.28 (complex m. 7H), 5.59 (s, 1H), 5.12 (s, 2H), 5.11-5.05 (m, 1H, $H_2$), 4.86 (dd, $J_{5,6}=4.4$ Hz, $J_{6,6'}=11.1$ Hz, 1H, $H_6$), 4.20 (t, $J_{6,6'}=J_{5,6'}=11.1$ Hz, 1H, $H_6$), 4.17 (dd, $J_{1,2}=4.1$ Hz, $J_{1,1'}=14.0$ Hz, 1H, $H_1$), 3.99 (dd, $J_{2,3}=6.2$ Hz, $J_{3,4}=9.0$ Hz, 1H, $H_3$), 3.84 (t, $J_{3,4}=J_{4,5}=9.0$ Hz, 1H, $H_4$), 3.50 (ddd, $J_{4,5}=9.0$ Hz, $J_{5,6}=4.4$ Hz, $J_{5,6'}=11.1$ Hz, 1H, $H_5$), 3.43 (dd, $J_{1',2}=7.7$ Hz, $J_{1,1'}=14.0$ Hz, 1H, $H_1'$), and 2.81 (br s, 1H, OH), 75 $^{13}$C NMR ($CDCl_3$) 165.9, 155.4, 137.2, 135.9, 133.5, 129.8, 129.4, 129.3, 128.6, 128.5, 128.4, 128.3, 128.1, 126.3, 102.0, 80.1, 74.1, 73.6, 69.5, 67.7, 53.1 and 45.2 ppm; mass spectrum (m/e) 496 (M+Li); and Anal. Calcd. for $C_{28}H_{27}NO_7$: C (68.70), H (5.55) and N (2.86); Found C (68.88), H (5.64) and N (2.70).

EXAMPLE 4

Preparation of N-Carbobenzoxy-2-O-benzoyl-4,6-O-benzylidene-1-deoxynojirimycin

Method B.

The stannylene intermediate from Example 2 (1.30 mmol) was placed under a nitrogen atmosphere, 5 mL of anhydrous methylene chloride was added, followed by 0.20 mL (150 mg, 1.48 mmol, 1.14 eq) of dry triethylamine and then 0.15 mL (183 mg, 1.30 mmol, 1.0 eq) of benzoyl chloride. After stirring at room temperature for one hour and fifteen minutes, an aqueous saturated sodium bicarbonate solution was added, the layer separated, the organic layer washed with 1N hydrochloric acid, dried with magnesium sulfate, filtered and concentrated to afford 0.93g of crude material. This was chromatographed on a 2 mm silica gel chromatatron plate using methylene chloride, 1% methanol/methylene chloride and 2% methanol/methylene chloride to afford 0.45 g (73%) of N-carbobenzoxy-2-O-benzoyl-4,6-O-benzylidene-1-deoxynojirimycin as a white solid, mp 118-120° C., whose spectra were identical to the material of Example 3.

EXAMPLE 5

Preparation of N-Carbobenzoxy-2-O-benzoyl-4,6-O-benzylidene-1,5-dideoxy-1,5-imino-D-allitol A 250 ml three-necked round-bottomed flask equipped with a nitrogen inlet, overhead stirrer, and rubber septum, was charged with 2.45 g (30.9 mmol) of distilled methyl sulfoxide and 50 mL of dry dichloromethane and cooled to −60° C. with a dry ice/acetone bath. To this was added dropwise over ca. 20 min. 5.63 g (26.8 mmol) of trifluoroacetic anhydride (a white precipitate should form). After an additional 10 min. of stirring was added a solution of 10.10 g (20.6 mmol) of N-carbobenzoxy-2-O-benzoyl-4,6-O-benzylidene-1-deoxynojirimycin in 50 mL of dichloromethane at a rate which maintains a −60° C. reaction temperature. The reaction was stirred an additional 50 min. at which time the bath was removed and the reaction was quenched immediately with 11.8 mL of triethylamine. The solution was allowed to warm to 0° C. and poured into 50 mL of dichloromethane. The solution was washed with 1.0 M HCl, saturated sodium bicarbonate and saturated brine, dried over magnesium sulfate, filtered and concentrated in vacuo, azeotroped with toluene, to yield 9.90 g of a white foamy oil which was identified as N-carbobenzoxy-2-O-benzoyl-4,6-O-benzylidene-3-keto-1-deoxynojirimycin; 300 MHz $^1$H NMR (d, $CDCl_3$) 8.10-7.30 (m, 15H), 5.67 (s, 1H), 5.54 (dd, $J_{1,2}=5.8$ Hz, $J_{1',2}=9.3$ Hz, 1H, $H_2$), 5.22 (dd, $g_{AB}=16.1$ Hz, $J_{AB}=11.7$ Hz, 2H, Z $CH_2$), 4.86 (dd, $J_{5,6}=5.6$ Hz, $J_{6,6'}=11.3$ Hz, 1H, $H_6$), 4.70 (dd, $J_{1,2}=5.7$ Hz, $J_{1,1'}=13.7$ Hz, 1H, $H_1$), 4.65 (d, $J_{4,5}=9.4$ Hz, 1H, $H_4$), 4.60 (t, $J_{5,6'}=10$ Hz, $J_{6,6'}=11.3$ Hz, 1H, $H_{6'}$), 3.74 (dt, $J_{4,5}=9.4$ Hz, $J_{5,6}=5.6$ Hz, $J_{5,6'}=10.0$ Hz, 1H, $H_5$) and 3.62 (dd, $J_{1,1'}=13.7$ Hz, $J_{1',2}=9.3$ Hz, 1H, $H_{1'}$).

The crude ketone was used without further purification. It was dissolved in 50 mL of methanol and 400 mL of tetrahydrofuran was added. The solution was cooled to −5° C. in an ice bath and 1.2 mL of acetic acid was added followed by 0.770 g (20.6 mmol) of sodium borohydride and stirred for 10 min. at which time another 0.770 g of sodium borohydride was added and stirred an additional 1 min. The reaction was quenched with 100 mL of saturated ammonium chloride and diluted with 25 mL of water to dissolve precipitate. The solution was extracted with 3×200 mL of ethyl acetate. The organic layer was dried over magnesium sulfate, filtered and concentrated in vacuo to yield a mixture of inverted allitol to glucitol of 2:1 with less than 10% migrated 3-O-benzoyl-allitol. The crude was subjected to $SiO_2$ chromatography, using dichloromethane: ethylacetate (95:5) as eluant to yield 3.36 g of desired allitol which was recrystallized from dichloromethane: hexanes to yield 3.36 g (34% yield) of white crystals which were identified as the desired allitol derivative, mp 143–144° C.; 300 MHz $^1$H NMR (d, $CDCl_3$) 8.08–7.30 (m, 15H), 5.56 (s, 1H), 5.13 (dd, $g_{AB}$=21.2 Hz, $J_{A,B}$=12.5 Hz, 2H, Z $CH_2$), 5.08 (ddd, $J_{1,2}$=5.0 Hz, $J_{1',2}$=11.8 Hz, $J_{2,3}$=3.0 Hz, 1H, $H_2$), 4.89 (dd, $J_{5,6}$=4.4 Hz, $J_{6,6'}$=11.7 Hz, 1H, $H_6$), 4.56 (t, $J_{5,6'}$=11.0 Hz, $J_{6,6'}$=11.7 Hz, 1H, $H_{6'}$), 4.50 (br s, 1H, $H_3$), 4.31 (dd, $J_{1,2}$=5.0 Hz, $J_{1,1'}$=12.7 Hz, 1H, $H_1$), 3.85 (dd, $J_{3,4}$=1.9 Hz, $J_{4,5}$=9.8 Hz, 1H, $H_4$), 3.78 (dt, $J_{5,6}$=4.4 Hz, $J_{4,5}$=9.8 Hz, $J_{5,6'}$=11.0 Hz, 1H, $H_5$) and 3.45 (dd, $J_{1',2}$=11.8 Hz, $J_{1,1'}$=12.7 Hz, 1H, $H_{1'}$); 75 MHz $^{13}$C NMR ($CDCl_3$) 165.5, 154.9, 137.2, 136.1, 133.4, 129.9, 129.6, 129.3, 128.6, 128.4, 128.3, 128.2, 126.1, 101.4, 77.9, 69.6, 68.9, 67.7, 67.6, 50.6, 43.6 ppm 496 (M+Li).

EXAMPLE 6

Preparation of
N-Carbobenzoxy-2-O-benzoyl-4,6-O-benzylidene-1,3-dideoxy-3-fluoronojirimycin To a solution of 3.31 g (6.7 mmol) of N-carbobenzoxy-2-O-benzoyl-4,6-O-benzylidene-1,5-dideoxy-1,5-imino-D-allitol in 20 mL of dichloromethane, 1.11 ml (14 mmol) of pyridine was added, the solution was cooled to −78° C. and 2.74 mL (20.7 mmol) of diethylaminosulfur trifluoride (DAST) was added dropwise over 5 min. The bath was removed and the reaction warmed gently to reflux for 16 hours, cooled to room temperature and quenched with saturated sodium bicarbonate. The solution was extracted with dichloromethane and washed with 1N HCl, saturated sodium bicarbonate, and brine, dried, filtered and concentrated. This was chromatographed on silica gel using 10% ethyl acetate/hexane as eluant, the desired fractions combined and recrystallized from methylene chloride/hexane to afford 1.92 g (60% yield) of N-carbobenzoxy-2-O-benzoyl-4,6-O-benzylidene-1,3-dideoxy-3-fluoronojirimycin as white needles, mp. 143–144° C.; 400 MHz $^1$H NMR (d, $CDCl_3$) 8.01 (d, J=8.0 Hz, 2H), 7.60–7.25 (m, 13H), 5.61 (s, 1H), 5.31 (dddd, $J_{1,2}$=3.7 Hz, $J_{1',2}$=8.0 Hz, $J_{2,3}$=5.9 Hz, $J_{2,1}$=17.2 Hz, 1H, $H_2$), 5.10 (s, 2H), 4.89 (ddd, $J_{5,6}$=4.4 Hz, $J_{6,6'}$=10.7 Hz, $J_{6,F}$=1.7 Hz, 1H, $H_6$), 4.80 (dt, $J_{3,F}$=51.1 Hz, $J_{2,3}$=5.9 Hz, $J_{3,4}$=8.5 Hz, 1H, $H_3$), 4.27 (t, $J_{5,6'}$=10.3 Hz, $J_{6,6'}$=10.7 Hz, 1H, $H_{6'}$), 4.22 (ddd, $J_{1,2}$=3.7 Hz, $J_{1,1'}$=13.9 Hz, $J_{1,F}$=2.4 Hz, 1H, $H_1$), 4.09 (ddd, $J_{3,4}$=8.5 Hz, $J_{4,5}$=10.5 Hz, $J_{4,F}$=18.7 Hz, 1H, $H_4$), 3.51 (ddd, $J_{5,6}$=4.4 Hz, $J_{4,5}$=10.5 Hz, $J_{5,6'}$=10.3 Hz, 1H, $H_5$) and 3.45 (dd, $J_{1',2}$=8.0 Hz, $J_{1,1'}$=13.9 Hz, 1H, $H_{1'}$); 101 MHz $^{13}$C NMR ($CDCl_3$) 165.1, 155.4, 137.0, 135.8, 133.6, 129.8, 129.3, 129.2, 128.7, 128.6, 128.4, 128.3, 128.1, 126.2, 101.6, 92.0 (d, $J_{C3,F}$=187.9 Hz, $C_3$), 78.1 (d, J=19.8 Hz), 70.5 (d, J=23.7 Hz), 69.6, 67.9, 52.5 (d, $J_{C5,F}$=7.3 Hz, $C_5$) and 45.1 (d, $J_{C1,F}$=5.3 Hz, $C_1$) ppm and mass spectrum (m/e) 498 (M+Li).

EXAMPLE 7

Preparation of N-Carbobenzoxy-4,6-O-benzylidene-1,3-dideoxy-3-fluoronojirimycin

To a solution of 1.92 g (3.9 mmol) of N-carbobenzoxy-2-O-benzoyl-4,6-O-benzylidene-1,3-dideoxy-3-fluoronojirimycin in 400 mL of dry methanol, 0.730 g (1.3 mmol) of sodium methoxide was added and the reaction stirred at room temperature under nitrogen atmosphere until the solution had cleared. An additional 500 mg of sodium methoxide was added before the reaction was complete by tlc (1% ethyl acetate, dichloromethane). The solution was neutralized with Dowex 50W-X8 resin (H form) and filtered immediately. The solvent was removed and the crude material was purified by silica gel chromatography using 1–3% ethyl acetate/methylene chloride as eluant to afford 1.10 g (73% yield) of the desired fluorohydrin; 400 MHz $^1$H NMR (d, $CDCl_3$) 7.50–7.30 (m, 10H), 5.58 (s, 1H), 5.12 (AB quartet, 2H), 4.82 (ddd, $J_{5,6}$=4.5 Hz, $J_{6,6'}$11.5 Hz $J_{6,F}$=2.0 Hz, 1H, $H_6$) 4.45 (dt $J_{3,F}$=52.3 Hz $J_{3,4}$=$J_{2,3}$=8.3 Hz, 1H, $H_3$), 4.44 (t, $J_{5,6'}$=10.5 Hz, $J_{6,6'}$=11.5 Hz, 1H, $H_{6'}$), 4.30 (dt, $J_{1,2}$=5.0 Hz, $J_{1,1'}$=13.5 Hz, $J_{1,F}$=5.0 Hz, 1H, $H_1$), 3.89 (dddd, $J_{1,2}$=5.0 Hz, $J_{2,3}$=8.3 Hz, $J_{1',2}$=10.3 Hz, 1H, $H_2$), 3.87 (ddd, $J_{3,4}$=8.3 Hz, $J_{4,5}$=10.1 Hz, $J_{4,F}$=12.6 Hz, 1H, $H_4$), 3.3 (dt, $J_{5,6}$=4.6 Hz, $J_{5,6'}$=$J_{4,5}$=10.1 Hz, 1H, $H_5$) and 2.88 (dd, $J_{1',2}$=10.2 Hz, $J_{1,1'}$=13.5 Hz, 1H, $H_{1'}$); 75 MHz $^{13}$C NMR ($CDCl_3$) 154.8, 137.0, 135.8, 129.3, 128.8, 128.6, 128.4, 128.3, 126.3, 101.4, 96.1 (d, $J_{C3,F}$=183 Hz) 78.2 (d, J=17.9 Hz); 69.2 (d, J=37 Hz) 68.3 (d, J=58 Hz) 54.25 (d, J=7.8 Hz) 48.4 (d, J=7.2 Hz).

EXAMPLE 8

Preparation of 1,3-Dideoxy-3-fluoronojirimycin

To a solution of 1.00 g (2.5 mmol) of N-carbobenzoxy-4,6-O-benzylidene-1,3-dideoxy-3-fluoronojirimycin in 50 mL of glacial acetic acid was added 225 mg of 10% Pd/C and the solution was subjected to 50 psig $H_2$, with stirring, for 72 hours. The solution was filtered through celite and concentrated in vacuo, azeotroped with toluene, and dried on a vacuum pump to yield 478 mg of acetate salt. The acetate was removed by passage through a 10 ml column of amberlite CG400 (OH form) resin and eluted with 75 mL of water. The solution was lyopholized and recrystallized from ethanol/hexane to yield 379 mg (80% yield) of 1,3-dideoxy-3-fluoronojirimycin, mp 163° C.; 500 MHz $^1$H NMR (d, $D_2O$) 4.26 (dt, $J_{3,F}$=53.2 Hz, $J_{2,3}$=$J_{3,4}$=9.2 Hz, 1H, $H_3$), 3.80 (br d, $J_{6,6'}$=11.7 Hz, 1H, $H_6$), 3.76 (dddd, $J_{1,2}$=5.5 Hz, $J_{1',2}$=11.9 Hz, $J_{2,3}$=9.0 Hz, $J_{2,F}$=5.3 Hz, 1H, $H_2$), 3.53 (dt, $J_{3,4}$=9.2 Hz, $J_{4,5}$=9.6 Hz, $J_{4,F}$=13.1 Hz, 1H, $H_4$), 3.14 (dt, $J_{1,2}$=5.4 Hz, $J_{1,1'}$=12.4 Hz, $J_{1,F}$=5.4 Hz, 1H, $H_1$), 2.60 (ddd, $J_{5,6}$3.0 Hz, $J_{5,6'}$=5.5 Hz, $J_{4,5}$=9.6 Hz, 1H, $H_5$) and 2.51 (t, $J_{1,2}$=12.0 Hz, $J_{1,1'}$=12.4 Hz, 1H, $H_{1'}$); 75 MHz $^{13}$C NMR ($D_2O$) 102.3 (d, $J_{C3,F}$=179.5 Hz, $C_3$), 72.8 (d, J=16.8 Hz), 72.4 (d, J=16.5 Hz), 63.8, 62.9 (d, $J_{C5,F}$=6.6 Hz) and 50.7 (d, $J_{C1,F}$=7.9 Hz, $C_1$) ppm; mass spectrum (m/e) 166 (M+H); and Anal. Calcd. for $C_6H_{12}FNO_3$: C (43.63), H (7.32) and N (8.48); Found C (43.85), H (7.41) and N (8.41).

EXAMPLE 9

Preparation of N-Butyl-1,3-dideoxy-3-fluoronojirimycin

To a solution of 340 mg (2.06 mmol) of 1,3-dideoxy-3-fluoronojirimycin in 10 mL of methanol was added 297 mg (364 ml, 2 eq.) of n-butyraldehyde. The solution was placed in a hydrogenation bottle containing 250 mg of 10% Pd/C and subjected to 5 psig. of $H_2$ for 24 hours with stirring. An additional 2 equivalents of butyraldehyde was added and the solution stirred an additional 48 hours. The catalyst was removed by filtration, and the solvent removed in vacuo. This material was chromatographed on silica gel using 10% ethanol/methylene chloride as eluent and then recrystallized from ethanol/hexanes to afford 380 mg (85% yield) of N-butyl-1,3-dideoxy-3-fluoronojirimycin, mp 116° C.; 500 MHz $^1$H NMR (d, $CD_3OD$) 4.01 (dddd, $J_{2,3}=8.9$ Hz, $J_{3,4}=9.2$ Hz, J=1.0 Hz, $J_{3,F}=53.6$ Hz, 1H, $H_3$), 3.84 (AB quartet, $J_{6,6'}=13.2$ Hz, 2H, $H_6$ and $H_{6'}$), 3.68 (dddd, $J_{1,2}=5.0$ Hz, $J_{1',2}=11.0$ Hz, $J_{2,3}=8.9$ Hz, $J_{2,F}=4.2$ Hz, 1H, $H_2$), 3.58 (dddd, $J_{3,4}=9.2$ Hz, $J_{4,5}=9.4$ Hz, J=1.0 Hz, $J_{4,F}=14.0$ Hz), 2.99 (dt, $J_{1,2}=5.0$ Hz, $J_{1,1'}=11.0$ Hz, $J_{1,F}=5.0$ Hz, 1H, $H_1$), 2.79 (dt, J=8.8 and 13.7 Hz, 1H), 2.56 (dt, J=7.8 and 13.7 Hz, 1H), 2.16 (t, $J_{1',2}=J_{1,1'}=11.0$ Hz, 1H, $H_{1'}$), 2.11 (br d, $J_{4,5}=9.4$ Hz, 1H, $H_5$), 1.45 (m, 2H), 1.31 (m, 2H) and 0.93 (t, J=7.0 Hz, 3H); 75 MHz $^{13}$C NMR ($CD_3OD$) 100.8 (d, $J_{C3,F}=181.4$ Hz, $C_3$), 69.9 (d, J=20.1 Hz), 69.0 (d, J=17.5 Hz), 66.8 (d, $J_{C5,F}=4.4$ Hz, $C_5$), 58.8, 56.8 (d, $J_{C1,F}=9.0$ Hz, $C_1$), 53.2, 27.5, 21.7 and 14.3 ppm; mass spectrum (m/e) 222 (M+H) and 204; and Anal. Calcd. for $C_{10}H_{20}FNO_3$: C (54.28), H (9.11) and N (6.33); Found C (54.21), H (9.14) and N (6.31).

EXAMPLE 10

Preparation of N-Carbobenzoxy-2-O-acetyl-4,6-O-benzylidene-1-deoxynojirimycin

To a mixture of 0.50 g (1.30 mmol) of N-carbobenzoxy-4,6-O-benzylidene-1-deoxynojirimycin and 0.34 g (1.36 mmol, 1.05 eq) of di-n-butyltin oxide (both dried in vacuo over $P_2O_5$ overnight) under nitrogen, was added 5 mL of dry methanol. After refluxing for two hours, the solution was cooled, concentrated, toluene added and removed twice under vacuum to afford a white solid. This was dissolved in 5 mL of anhydrous methylene chloride under a nitrogen atmosphere adn 0.20 mL (0.15 g, 1.43 mmol, 1.10 eq) of dry triethyl-amine, followed by 92 ml (102 mg, 1.29 mmol, 1.0 eq) of acetyl chloride. After stirring at room temperature for one hour, 1N hydrochloric acid was added, the organic layer separated, dried with magnesium sulfate, filtered and concentrated under vacuum to afford 0.89 g of an oil, whose $^1$H NMR spectrum indicated a 90:10 mixture of the 2-O-acetyl and 3-O-acetyl derivatives, respectively. Chromatography on a 2 mm silica gel chromatatron plate using methylene chloride, 1% methanol/methylene chloride, 2% methanol/methylene chloride and 5% methanol/methylene chloride afforded 0.24 g (44%) of N-=carbobenzoxy-2-O-acetyl-4,6-O-benzylidene-1-deoxynojirimycin as a white foam; 300 MHz $^1$H NMR (d, $CDCl_3$) 7.52-7.30 (complex m, 10H), 5.56 (s, 1H), 5.12 (AB quartet, $J_{AB}=12.3$ Hz, $u_{AB}19.8$ Hz, 2H), 4.89-4.78 (complex m, 2H, $H_2$ and $H_6$), 4.23 (t, $J_{6,6'}=10.7$ Hz, 1H, $H_{6'}$), 4.12 (dd, $J_{1,2}=4.4$ Hz, $H_{1,1'}=13.9$ Hz, 1H, $H_1$), 3.79 (br t, $J_{2,3}=J_{3,4}=9.7$ Hz, 1H, $H_3$), 3.71 (t, $J_{3,4}=J_{4,5}=9.7$ Hz, 1H, $H_4$), 3.38 (ddd, $J_{5,6}=4.4$ Hz, $J_{4,5}=J_{5,6'}=9.7$ Hz, 1H, $H_5$), 3.17 (dd, $J_{1',2}=8.1$ Hz, $J_{1,1'}=13.9$ Hz, 1H, $H_{1'}$) and 2.80 (br s, 1H, OH); 75 MHz $^{13}$C NMR ($CDCl_3$), 170.4 (C), 155.2 (C), 137.1 (C), 136.0 (CO), 129.4 (CH), 128.7 (CH), 128.4 (CH), 128.3 (CH), 128.1 (CH), 126.3 (CH), 101.9 (CH), 80.1 (CH), 74.0 (CH), 69.4 ($CH_2$), 67.7 ($CH_2$, 53.5 (CH), 45.5 ($CH_2$) and 20.9 ($CH_3$) ppm; and mass spectrum (m/e) 434 (M+Li).

EXAMPLE 11

Preparation of N-Carbobenzoxy-2-O-benzyl-4,6-O-benzylidene-1-deoxynojirimycin

To a mixture of 10.0 g (0.0260 mmol) of N-carbobenzoxy-4,6-O-benzylidene-1-deoxynojirimycin and 6.79 g (0.0273 mol) of dibutyl tin oxide, under nitrogen atmosphere, was added 100 mL of dry methanol and the mixture refluxed for three hours. After cooling to room temperature, the solvent was removed in vacuo. The crude foam was further dried by 2×100 mL toluene azeotropes to yield 16.0 g (99% yield) of N-carbobenzoxy-4,6-O-benzylidene-2,3-O-(di-n-butylstannylene)-1-deoxynojirimycin. The crude stannylene was dissolved in 65 mL (0.4 M) of acetonitrile and to this was added 2.0 g (20 mol %) of tetra-n-butylammonium iodide and 4.5 mL (1.5 eq) of benzylbromide and the mixture refluxed for 24 hours. After cooling, the solvents were removed in vacuo to yield 11.5 g (94%) of 3:1 mixture of 2-O-benzyl and 3-O-benzyl products, respectively. The mixture was chromatographed on a flash column (silica) using 0.5% methanol, 99.5% methylene chloride eluant to yield 4.5 g of pure N-carbobenzoxy-2-O-benzyl-4,6-O-benzylidene-1-deoxynojirimycin (38% yield), mp 112.5° C.; 300 MHz $^1$H NMR (d, $CDCl_3$), 7.51-7.27 (m, 15H), 5.53 (s, 1H), 5.10 (s, 2H), 4.78 (dd, $H_{5,6}=4.5$ Hz $H_{6,6'}=10.8$ Hz, 1H, $H_6$), 4.67 (s, 2H), 4.28 (t, $J_{5,6'}=J_{6,6'}=10.8$ Hz, 1H, $H_{6'}$), 4.15 (dd, $J_{1,1'}$-13.5 Hz, $J_{1,2}=4.1$ Hz, 1H, $H_1$), 3.79 (dd, $J_{2,3}=7.0$ Hz, $J_{3,4}=8.7$ Hz, 1H, $H_3$), 3.64 (t, $J_{4,5}=J_{3,4}=8.7$ Hz, 1H, $H_4$), 3.48 (ddd, $J_{1,2}=4.1$ Hz, $J_{1',2}=9.1$ Hz, $J_{2,3}=7.0$ Hz, 1H, $H_2$), 3.33 (ddd, $J_{5,6}=4.5$ Hz, $J_{5,6}=10.3$ Hz, $J_{4,5}=8.7$ Hz, 1H, $H_5$) and 3.01 (dd, $J_{1,1'}=13.5$ Hz, $J_{1',2}=9.1$ Hz, 1H, $H_{1'}$); 75 MHz $^{13}$C NMR (CDCl ) 155.1, 137.9, 137.3, 136.1, 129.4, 129.4, 129.3, 129.3, 129.2, 128.7, 128.6, 128.7, 128.4, 128.3, 128.2, 127.9, 127.8, 127.8, 126.3, 101.8, 80.4, 75.8, 72.3, 69.6, 67.6, 54.0 and 46.5; and mass spectrum (m/e) 482 (M+Li).

EXAMPLE 12

This example illustrates glycosidase inhibition activity for 1,3-dideoxy-3-fluoronojirimycin (1) and N-butyl-1,3-dideoxy-3-fluoronojirimycin (2). It is contemplated that other N-derivatives will also manifest glycosidase inhibition activity.

The glycosidase inhibition activity is determined by modifying an assay procedure described in Evans et al, Phytochemistry, 22, pp. 768-770 (1983). More particularly, yeast α-glucosidase and almond β-glucosidase activities were measured by the Evans et al method which was modified by assaying activities at pH 7.4 in N-2-hydroxyethylpiperazine-N-2-ethane sulfonic acid (HEPES) buffer, measuring in 96 well microtiter plates, and including 10% DMSO in control and test samples.

The release of p-nitrophenol from the substrate p-nitrophenylglycoside was measured spectrophotometrically in the presence and absence of test compound.

Each assay included a known inhibitor of the enzyme as a standard. IC$_{50}$ values were determined for compounds which inhibited the enzymes more than 50% at a 1 millimolar concentration.

α-Glucosidase Inhibition Assay, pH 7.4

To 100 ul 50 mM HEPES buffer, pH 7.4, in a microtiter plate, 20 ul test compound in DMSO (DMSO alone in control) and 40 ul (0.013 units) yeast α-glucosidase (Sigma) in HEPES buffer were added and pre-incubated at room temperature 15 minutes. 40 ul 1.25 mM p-nitrophenyl-α-D-glucopyranoside (Sigma) in HEPES buffer, as substrate was added and the absorbance change at 405 nm was monitored in a Biotek EIA Autoreader. Absorption change was measured at 15 to 25 minutes (reaction was linear for at least 30 minutes). Each sample was tested in triplicate. IC$_{50}$ values were determined from the linear portion of the log concentration vs percent inhibition curve obtained from a minimum of 3 points. Deoxynojirimycin was used as standard inhibitor.

β-Glucosidase Inhibition Assay pH 7.4:

To 100 ul 50 mM HEPES buffer, pH 7.4, in a microtiter plate, 20 ul test compound in DMSO (DMSO alone in control) and 40 ul (0.136 units) β-glucosidase (Sigma) in HEPES buffer were added and pre-incubated at room temperature 15 minutes. 40 ul 1.25 mM p-nitrophenyl-β-D-glucopyranoside in HEPES buffer was added as substrate and the absorbance change at 405 nm was monitored utilizing a Biotek EIA Autoreader. Absorption change was measured at 15 to 25 minutes (reaction is linear for at least 30 minutes). Each sample was tested in triplicate. IC$_{50}$ values were determined from the linear portion of the log concentration vs percent inhibition curve obtained from a minimum of 3 points. Castanospermine was used as standard inhibitor.

pH 4.8:

To 100 ul 50 mM sodium citrate buffer, pH 4.8, in a microtiter plate, 20 ul test compound in DMSO (DMSO alone in control) and 20 ul (0.017 units) β-glucosidase (Sigma) in citrate buffer were added and pre-incubated at room temperature 15 minutes. 20 ul 2.50 mM p-nitrophenyl-β-D-glucopyranside in citrate buffer was added as substrate and incubated at room temperature 20 minutes (reaction is linear for at least 30 minutes). 50 ul 0.4 M NaOH was added and the absorption change at 405 nm was determined utilizing a Biotek EIA Autoreader. Each sample was tested in triplicate. IC$_{50}$ values were determined from the linear portion of the log concentration vs percent inhibition curve obtained from a minimum of 3 points. Castanospermine was used as standard inhibitor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound represented by the formula:

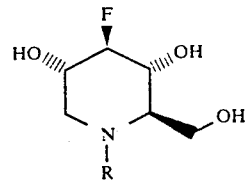

wherein R represents hydrogen, alkyl radicals having from 1 to about 10 carbon atoms, alkenyl radicals having from 2 to about 10 carbon atoms, aryl, alkaryl and aralkyl radicals having from about 6 to about 16 carbon atoms and radicals represented by the formula:

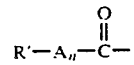

wherein R' represents alkyl radicals, having from about 1 to about 10 carbon atoms, and aryl, aralkyl and alkaryl radicals having from about 6 to about 26 carbon atoms, A represents oxygen, and n is 0 or 1.

2. Compound of claim 1 wherein R represents hydrogen.
3. Compound of claim 1 wherein R represents an alkyl radical having from 1 to about 10 carbon atoms.
4. Compound of claim 1 wherein R represents an alkyl radical having from 1 to about 6 carbon atoms.
5. Compound of claim 1 wherein R represents an alkyl radical having 4 carbon atoms.
6. Compound of claim 1 wherein R is n-butyl.
7. N-butyl-1,3-dideoxy-3-fluoronojirimycin.
8. 1,3-dideoxy-3-fluoronojirimycin.
9. Composition for inhibiting glycosidase activity comprising a compound of claim 1 and a pharmaceutically acceptable diluent and/or carrier.
10. Compound represented by the formula:

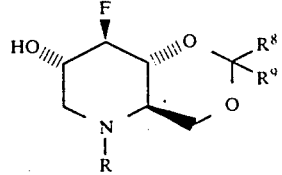

TABLE 1

| | | Enzyme Inhibition Data | | | |
|---|---|---|---|---|---|
| COMPOUND NO. | ALPHA GLUCOSIDASE | BETA GLUCOSIDASE-pH 4.8 | BETA GLUCOSIDASE-pH 7.4 | ALPHA MANNOSIDASE-pH 4.5 | ALPHA MANNOSIDASE-pH 7.4 |
| 1 | 26% @ 1 mM | 4% @ 1 mM | 3% @ 1 mM | 11% @ 1 mM | 10% @ 1 mM |
|   | 63% @ 5 mM | 10% @ 5 mM | 24% @ 5 mM | 19% @ 5 mM | 30% @ 5 mM |
| 2 | 11% @ 1 mM | 8% @ 1 mM | 0% @ 1 mM | 6% @ 1 mM | 7% @ 1 mM |
|   | 18% @ 5 mM | −10% @ 5 mM | 2% @ 5 mM | 5% @ 5 mM | 11% @ 5 mM | wherein R represents hydrogen, alkyl radicals having from 1 to about 10 carbon atoms, alkenyl radicals having from 2 to about 10 carbon atoms, aryl, aralkyl and alkaryl radials having from about 6 to about 16 carbon atoms and radicals represented by the formula:

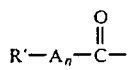

wherein R' represents alkyl radicals, having from 1 to about 10 carbon atoms, and aryl, aralkyl and alkaryl radicals having from about 6 to about 26 carbon atoms, A represents oxygen, and n is 0 or 1; and $R^8$ and $R^9$ independently represent hydrogen, alkyl radicals having from 1 to about 10 carbon atoms and aryl radicals.

11. Compound of claim 10 wherein R represents hydrogen.

12. Compound of claim 10 wherein R represents an alkyl radical having from 1 to about 10 carbon atoms.

13. Compound of claim 10 wherein R represents an alkyl radical having from 1 to about 6 carbon atoms.

14. Compound of claim 10 wherein R represents an alkyl radical having 4 carbon atoms.

15. Compound of claim 10 wherein R is n-butyl.

16. Compound of claim 10 wherein R represents a carbobenzoxy radical.

17. Compound of claim 10 wherein R represents a butyryl radical.

18. Composition for inhibiting glycosidase activity comprising a compound of claim 10 and a pharmaceutically acceptable diluent and/or carrier.

19. Compound represented by the formula:

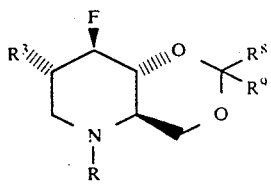

wherein R represents hydrogen, alkyl radicals having from 1 to about 10 carbon atoms, alkenyl radicals having from 2 to about 10 carbon atoms, aryl, aralkyl and alkaryl radials having from about 6 to about 16 carbon atoms and radicals represented by the formula:

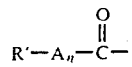

wherein R' represents alkyl radicals, having from 1 to about 10 carbon atoms, and aryl, aralkyl and alkaryl radicals having from about 6 to about 26 carbon atoms, A represents oxygen, and n is 0 or 1; $R^3$ represents benzyl and allyl ethers, and acyl esters represented by the formula

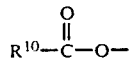

wherein $R^{10}$ represents alkyl radicals having from 1 to about 10 carbon atoms and aryl, aralkyl and alkaryl radicals; and $R^8$ and $R^9$ independently represent hydrogen, alkyl radicals having from 1 to about 10 carbon atoms and aryl radicals.

20. Compound of claim 19 wherein R represents hydrogen.

21. Compound of claim 19 wherein R represents an alkyl radical having from 1 to about 10 carbon atoms.

22. Compound of claim 19 wherein R represents an alkyl radical having from 1 to about 6 carbon atoms.

23. Compound of claim 19 wherein R represents an alkyl radical having 4 carbon atoms.

24. Compound of claim 19 wherein R is n-butyl.

25. Compound of claim 19 wherein R represents a carbobenzoxy radical.

26. Compound of claim 19 wherein R represents a butyryl radical.

27. Composition for inhibiting glycosidase activity comprising a compound of claim 19 and a pharmaceutically acceptable diluent and/or carrier.

* * * * *